United States Patent [19]

Schellenbaum et al.

[11] 3,944,652

[45] Mar. 16, 1976

[54] MICROBICIDAL AGENTS CONTAINING AS ACTIVE INGREDIENT MONOHYDROXYPHENYL CARBINOLS

[75] Inventors: Max Schellenbaum, Muttenz; Max Duennenberger, Frenkendorf; Fulvio Casagrande, Binningen, all of Switzerland

[73] Assignee: Ciba-Geigy, Basel, Switzerland

[22] Filed: Feb. 26, 1975

[21] Appl. No.: 553,350

Related U.S. Application Data

[62] Division of Ser. No. 164,446, July 20, 1971, Pat. No. 3,879,479.

[30] Foreign Application Priority Data

July 23, 1970 Switzerland.......................... 11172/70

[52] U.S. Cl. ............... 424/345; 106/125; 106/162; 162/161; 260/92.8 A; 428/500

[51] Int. Cl.$^2$............................................ A01N 9/24
[58] Field of Search...................................... 424/345

[56] References Cited
UNITED STATES PATENTS

| | | | |
|---|---|---|---|
| 2,709,704 | 5/1955 | Brown.......................... | 260/618 B X |
| 2,798,088 | 7/1957 | Ritter et al.................. | 260/618 H X |
| 2,895,871 | 7/1959 | Entemann.................... | 260/618 B X |
| 2,945,886 | 7/1960 | Brown.......................... | 260/618 H X |
| 3,479,294 | 11/1969 | Week............................ | 260/619 R |

*Primary Examiner*—Jerome D. Goldberg
*Assistant Examiner*—Allen J. Robinson
*Attorney, Agent, or Firm*—Frederick H. Rabin

[57] ABSTRACT

Monohydroxyphenyl carbinols with at least two halogen atoms in the molecule have been found as microbicides which are effective against various types of bacteria and fungi.

17 Claims, No Drawings

MICROBICIDAL AGENTS CONTAINING AS ACTIVE INGREDIENT MONOHYDROXYPHENYL CARBINOLS

This is a division of application Ser. No. 164,446, filed on July 20, 1971, now U.S. Pat. No. 3,879,479, issued Apr. 22, 1975.

This invention relates to monohydroxyphenyl carbinols, their manufacture and use.

According to the present invention there are provided monohydroxyphenyl carbinols of the general formula

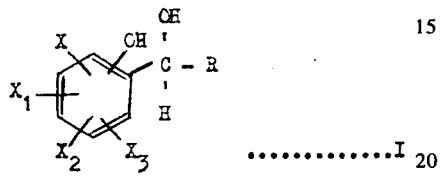

wherein
X is halogen,
$X_1$, $X_2$ and $X_3$ are each halogen or hydrogen, and
R is a straight or branched chain alkyl group of 1–8 carbon atoms,
or cycloalkyl group of 3–8 carbon atoms or phenyl, unsubstituted or substituted by halogen and/or alkyl of 1–2 carbon atoms, there being at least 2 halogen atoms in the molecule.

These compounds possess microbicidal activity.

The hydroxyl group is formula I is preferably in 2- or 4- position. The most important cycloalkyl groups are cyclopentyl and, especially, cyclohexyl.

The alkyl groups can be, for example, methyl, ethyl and all isomers of propyl, butyl, amyl, hexyl, heptyl and octyl. Halogen includes bromine and chlorine.

Formula I includes hydroxyphenyl carbinols of the formula

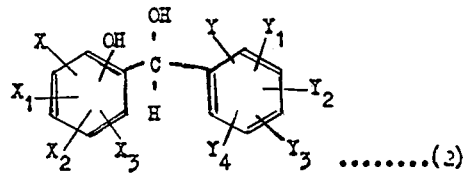

wherein X, $X_1$, $X_2$ and $X_3$ have the meanings given above, and Y and $Y_1$ are each methyl, halogen or hydrogen. $Y_2$, $Y_3$ and $Y_4$ are each halogen or hydrogen, there being at least 2 halogen atoms in the formula, and the phenolic hydroxy group being in the 2- or 4- position to the carbinol bridge, as well as hydroxyphenyl alkyl carbinols of the formula

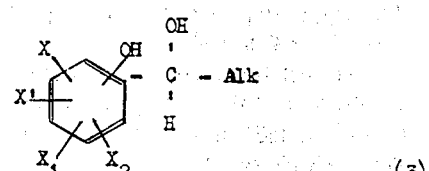

wherein X' is halogen and Alk is straight or branched chain alkyl of 1–8 carbon atoms, and X, $X_1$ and $X_2$ have the meaning given above, wherein the hydroxy group is in 2- or 4- position to the carbinol bridge.

In the compounds of formula 2 there are generally never more than 6 halogen atoms.

Among the compounds of formula 3, the 2-hydroxyphenyl derivatives are particularly notable. Preferred alkyl groups have 3–7 carbon atoms, these groups being preferably unbranched.

Particularly interesting microbicidal are those 2-hydroxyphenyl alkyl carbinols of formula 3 wherein X and X' are the same and are chlorine or bromine, while $X_1$ and $X_2$ are hydrogen and Alk is n-butyl or n-amyl.

Furthermore, of great particular interest are monohydroxybenzhydrels of the formula

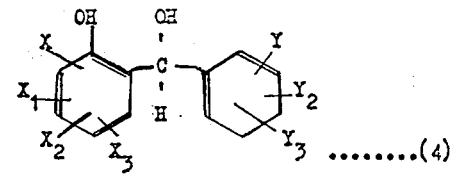

wherein X, $X_1$, $X_2$, $X_3$, Y, $Y_2$ and $Y_3$ have the meanings given above and wherein at least two of $X_1$, $X_2$, $X_3$, Y, $Y_2$ and $Y_3$ are different from hydrogen.

Within the scope of formula 4 are compounds of particular interest and of the formula

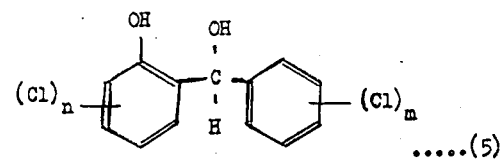

wherein $n$ is 2, 3 or 4, and $m$ is 1, 2 or 3, and $n + m$ is 3, 4 or 5.

The most important 4-hydroxybenzhydrols are given by the formula

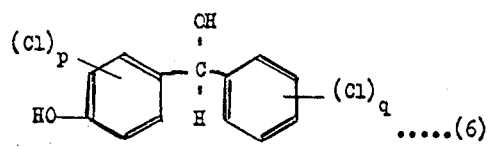

wherein $p$ and $q$ are each 1, 2 or 3 and $p + q$ is 3 or 4.

In order to manufacture the monohydroxphenyl carbinols of the invention, a ketone of the formula

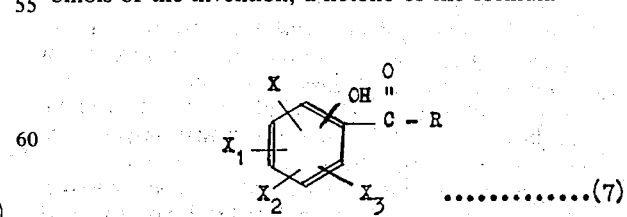

wherein X, $X_1$, $X_2$, $X_3$ and R have the meanings given above is reduced. The compounds of formulae 2 to 6 can be made from ketones of the formula (8) 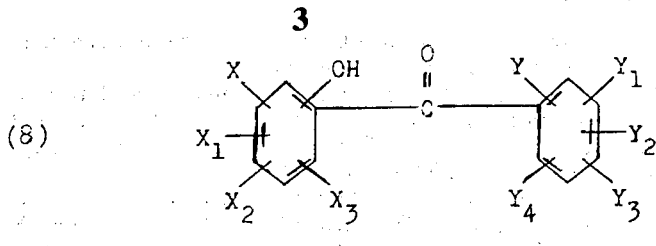

(9) 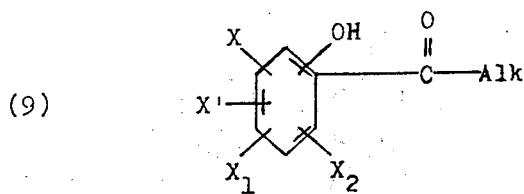

(10) 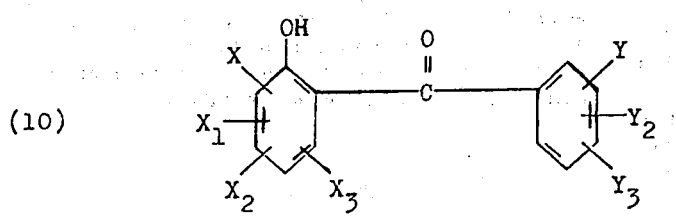

(11) 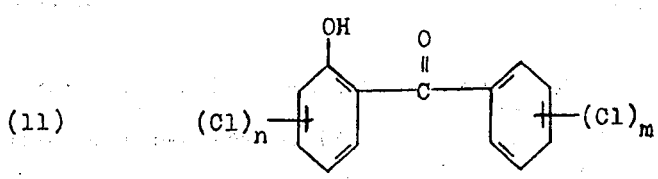

and 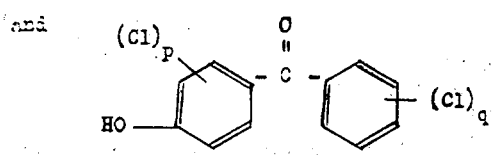

wherein the various symbols have the meanings given above, and the numbers of substituents and position of the hydroxy group are as given above also.

As reducing agent, for example a hydride can be used, the reaction being carried out in a solvent medium inert to the hydride.

For this, sodium borohydride is used with advantage, generally 0.25 – 1 mol per mol of the hydroxyphenyl ketone to be reduced, corresponding to 1 to 4 equivalents. Particularly good yields are obtained if a polar solvent is used such as water, methanol, ethanol, isopropanol or dioxane, or mixtures of these solvents such as a water/methanol mix. The hydroxyphenyl ketone to be reduced is generally subjected to reaction in the form of a phenolate, i.e. in salt form, preferably an alkali salt such as the ammonium, potassium or, particularly the sodium salt.

The reaction temperature may vary for example between 0°C and the boiling temperature of the solvent used. The reaction time is correspondingly generally 20 to 1 hours.

Further reduction methods which can be used are reduction with zinc dust in alcoholic alkali hydroxide solution, for example potassium hydroxide or sodium hydroxide, and reduction by means of sodium amalgam in alcoholic solution or by means of aluminium isopropylate in isopropanolic solution (the method of Meerwein-Ponndorf-Verley).

Note should also be taken of the catalytic hydrogenation of hydroxphenyl ketones to give the hydroxyphenyl carbinols of the present invention.

The hydroxyphenyl ketones used as starting products are known (see Belgian Pat. Specifications No. 753,533 and 753,534) or are manufactured by methods known per se, for example from the corresponding benzoic acid or alkane carboxylic acid phenyl esters by the Fries reaction (compare "Baltzly et al. Journal of the American Chemical Society 77, 2522 (1955)," "L. F. and M. Fieser, Lehrbuch der organischen Chemie 1954, page 723" or "G. A. Olah, Friedel-Crafts and Related Reactions 1964, page 499"). The reaction can take place in the molten state or in the presence of an organic solvent medium, e.g. nitrobenzene. On heating the corresponding phenyl ester together with aluminium chloride there results the monohydroxybenzophenone or monohydroxyphenylalkyl ketone.

Particularly surprising for the compounds according to the invention is the broad spectrum of anti-bacterial activity, which for most of the compounds extends both over the area of gram-positive and gram-negative bacteria. From an application point of view, the lack of smell and the colourlessness of the compounds of the invention is of particular value.

The present invention includes quite generally the use of the compounds according to the invention in pest combating. The use of the anti-microbial compounds is possible on a very wide basis, particularly for the protection of organic substrates against attack by destructive and pathogenic micro organism (including phytopathogenic ones). The anti-microbial agents noted are also suitable both as a preserving agent and as a disinfectant for technical products of all types, for plant protection, in farming, in veterinary medicines and in cosmetic technology.

The monohydroxybenzhydrols according to the invention are thus used for treating or protecting organic materials, particularly textiles, by impregnating at least one of these compounds into the material to be treated or protected or by applying such to the surface of the materials.

Among non-textile technical products which can be preserved with the aid of compounds according to the invention, the following examples should be noted:

Glues, binding agents, coating agents, textile dressings and treating agents, printing and colouring pastes and similar preparations on the basis of organic and inorganic dyes or pigments, also those which contain in admixture casein or other organic compounds. Also wall and ceiling coatings, e.g. such as have an albumen containing colour binding agent, are protected by addition of a compound according to the invention from attack by pests. Use for wood protection is likewise possible.

In the cellulose and paper industry also, the compounds according to the invention can be used as conservation agents, inter alia for preventing the known slime formation generated by micro organism infestation in the apparatus and machinery used for papermaking.

Furthermore by combination of the monohydroxybenzhydrols of the invention with surface active agents, particularly washing active agents it is possible to produce washing and cleaning agents with exceptional anti-bacterial or anti-mycotic action. The compounds according to the invention can, for example, be blended into soaps or combined with soap-free washing agents or other surface active materials, particularly non-ionic and cationic washing agents, or they can be combined together with mixtures of soaps and soap-free washing materials, wherein in these combinations their anti-microbial effectiveness is retained to the fullest degree. By the use of aqueous preparations of such washing and cleaning agents containing monohydroxybenzhydrols according to the invention, textile materials, for example, can be treated anti-microbially during washing, since the active agent is substantive to the textile material.

Cleaning agents which contain the compounds of the above noted formulae can be used both in industrial and domestic use, also in foodstuff industries e.g. dairies, breweries and slaughter houses. The present compounds can also be used as a component of preparations which are used for cleaning or disinfection.

The action of the monohydroxybenzhydrols according to the invention can also be used in conserving and disinfecting preparations for plastics materials. In the use of plasticisers it is advantageous to add the antimicrobial addition to the plastics material dissolved or dispersed in the plasticiser. It is advisable to take pains to obtain as even as possible a distribution in the plastic material. The plastics materials with anti-microbial properties can be used for useful articles of all types in which an effectiveness against varied germs, e.g. bacteria and fungi, is desired, thus for example in foot mats, bath curtainings, seats, steps in swimming baths, wall coverings, etc. By incorporation into suitable waxing and polishing compositions, suitable floor cleaning and furniture care materials with disinfectant action can be produced.

Furthermore the compounds according to the invention can be used for the conserving and disinfecting treatment of fibres and textiles, wherein they can be applied to both natural and synthetic fibres and there effect a permanent action against harmful (and pathogenic) micro organism, for example fungi and bacteria. The addition of these compounds can take place therein before simultaneously with or after the treatment of these textiles with other materials e.g. printing or dyeing pastes, dressings, etc.

Textiles treated in this way also are protected against the generation of a sweaty smell as is generated by micro organisms.

Treatment can take place for example by impregnating or spraying with solutions or suspensions containing the above noted compounds as active agent. The active agent can vary according to the purpose of use between 0.1 and 50 grams active substance per liter, preferably 1 – 30 grams.

Generally textile materials of both synthetic or natural origin can be satisfactorily protected against attack by mould fungi or bacteria by a content of from 0.1 to 3% of active agent. The active agent noted can be added together with other textile treatment agents as dressing agents, permanent creasing treatments etc.

The ways of using the active agents of the present invention can correspond to the usual formulations for pest control agents, for example, agents which contain the said active agent can optionally also contain additives such as solvents, dispersing agents, wetting agents, adhesives, light protection agents, optical brighteners etc., together with other pest control agents, such as fungicides and bactericides. Particularly, however, as well as the active agent according to the invention, the agent can contain a further solid or liquid thinning agent or a solid or liquid carrier. The invention extends to microbicidal agents which contain compounds of the general formula I.

The following examples will serve to Illustrate the invention.

EXAMPLE 1

A. To a solution of 1.2 grams sodium hydroxide in 10 ml water and 50 ml methanol there was added 9.0 g 2-hydroxy-5,3',4'-trichlorobenzophenone and 0.6 g sodiumborohydride. The reaction solution was kept for 5 hours at 25°C with stirring. After addition of 50 ml 2-n-hydrochloric acid the product was extracted with ethyl acetate and the extract washed first with saturated potassium bicarbonate solution and then with water. The extract dried over sodium sulphate left behind 8.6 g of the compound of formula

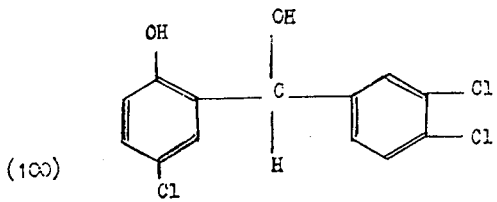

which was an oil which crystallised on standing; melting point 120°–128°C.

The purified compound from recrystallisation from chloroform melted at 130°–131°C. The pure yield amounted to 7.3 g.

B. To 31 g aluminiumisopropylate in 150 ml isopropanol there was added a solution of 9.0 g 2-hydroxy-5,3',4',-trichlorobenzophenone in 25 ml isopropanol. The reaction mixture was then boiled under reflux for 20 hours. After the addition of 150 ml 2-n-hydrochloric acid at 25°C, the product was extracted with ethyl acetate and the extract washed first with saturated potassium bicarbonate solution and then with water. From the extract which was dried over sodium sulphate there remained after the removal of the solvent 8.5 g of the compound 100 as an oil which crystallised on standing.

After recrystallisation from chloroform the compound was present in pure form and melted at 130°–131°C.

In the same way as example 1 or according to one of the other methods given above the following compounds can be prepared which are shown in the following table A:

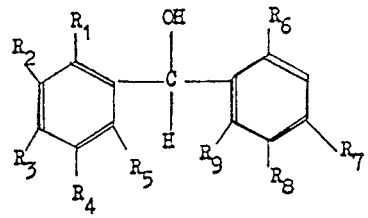

TABLE A

| Compound No. | $R_1$ | $R_2$ | $R_3$ | $R_4$ | $R_5$ | $R_6$ | $R_7$ | $R_8$ | $R_9$ | Melting point in °C |
|---|---|---|---|---|---|---|---|---|---|---|
| 100 | OH | H | H | Cl | H | H | Cl | Cl | H | 131 – 132 |
| 101 | OH | H | H | Cl | H | H | Cl | H | H | 102 – 104 |
| 102 | OH | H | Cl | H | H | H | Cl | H | Cl | < 30 |
| 103 | OH | Cl | H | Cl | H | H | Cl | Cl | H | 155 – 157 |
| 104 | OH | H | H | Cl | H | H | Cl | H | Cl | 110 – 112 |
| 105 | OH | Cl | H | Cl | H | H | Cl | H | H | 93 – 94 |
| 106 | OH | Cl | H | Cl | H | H | Cl | H | Cl | 106 – 107 |
| 107 | OH | Cl | H | Cl | Cl | H | Cl | H | Cl | 133 – 134 |
| 108 | OH | Cl | H | Cl | Cl | H | Cl | H | H | 176 – 178 |
| 109 | OH | H | Cl | H | Cl | H | Cl | Cl | H | 145 – 146 |
| 110 | OH | H | Cl | H | H | H | Cl | Cl | H | 106 – 107 |
| 111 | OH | Cl | H | Cl | Cl | H | Cl | Cl | H | 189 – 190 |
| 112 | OH | H | H | Cl | Cl | H | Cl | Cl | H | Oil |
| 113 | OH | H | H | Br | H | H | Cl | Cl | H | 134 – 135 |
| 114 | OH | Br | H | Br | H | H | Cl | Cl | H | 124 – 125 |
| 115 | OH | H | Cl | H | Cl | Cl | Cl | H | H | 135 – 136 |
| 116 | OH | H | Cl | Cl | H | Cl | Cl | H | H | 119 – 120 |
| 117 | OH | H | Br | H | Cl | Cl | Cl | H | H | 103 – 104 |
| 118 | OH | Br | H | Br | H | Cl | Cl | H | H | 278 – 279 |
| 119 | OH | H | Cl | H | Cl | Cl | H | Cl | H | 146 – 147 |
| 120 | OH | H | Cl | H | H | Cl | H | Cl | H | 135 – 136 |
| 121 | OH | Cl | H | Cl | Cl | Cl | H | Cl | H | 156 – 157 |
| 122 | OH | H | Cl | Cl | H | Cl | H | Cl | H | 182 – 183 |
| 123 | OH | H | Cl | H | Cl | Cl | H | H | Cl | 175 – 176 |
| 124 | OH | Cl | H | Cl | Cl | Cl | H | H | Cl | 189 – 190 |
| 125 | OH | H | Cl | Cl | H | Cl | H | H | Cl | 156 – 157 |
| 126 | OH | H | Cl | Cl | H | H | Cl | H | H | 98 – 99 |
| 127 | OH | H | Cl | Cl | H | Cl | $CH_3$ | H | H | 115 – 116 |
| 128 | OH | H | Cl | H | H | $CH_3$ | H | H | H | 131 – 132 |
| 129 | OH | Cl | H | Cl | Cl | $CH_3$ | H | H | H | 153 – 154 |
| 130 | OH | H | Cl | H | Cl | Cl | H | H | H | 99 – 100 |
| 131 | OH | H | Cl | H | H | Cl | H | H | H | 114 – 115 |
| 132 | OH | H | H | Cl | H | Cl | H | H | H | 97 – 98 |
| 133 | OH | Cl | H | Cl | H | Cl | H | H | H | 78 – 79 |
| 134 | OH | Cl | H | Cl | Cl | Cl | H | H | H | 123 – 124 |
| 135 | OH | H | Cl | Cl | H | Cl | H | H | H | 109 – 110 |
| 136 | OH | Cl | H | Cl | H | H | H | H | H | 94 – 95 |
| 137 | OH | Cl | H | Cl | Cl | H | H | H | H | 168 – 169 |
| 138 | OH | Br | H | Br | H | H | H | H | H | 121 – 122 |
| 139 | OH | Cl | H | Cl | Cl | H | $CH_3$ | H | H | 175 – 176 |
| 140 | OH | Cl | H | Cl | Cl | H | Br | H | H | 178 – 179 |
| 141 | OH | Br | H | Br | H | H | Br | H | H | 135 – 136 |
| 142 | OH | H | H | Br | H | H | Cl | H | H | 105 – 106 |
| 143 | OH | Br | H | Br | H | H | Cl | H | H | 116 – 117 |
| 144 | H | H | OH | Cl | H | Cl | Cl | Cl | H | 144 – 145 |
| 145 | H | Cl | OH | Cl | H | H | Cl | H | H | 165 – 167 |

TABLE A-continued

| Compound No. | $R_1$ | $R_2$ | $R_3$ | $R_4$ | $R_5$ | $R_6$ | $R_7$ | $R_8$ | $R_9$ | Melting point in °C |
|---|---|---|---|---|---|---|---|---|---|---|
| 146 | H | Cl | OH | Cl | H | H | Cl | Cl | H | 175 – 176 |
| 147 | H | Cl | OH | Cl | H | H | Br | H | H | 159 – 160 |
| 148 | H | Cl | OH | H | Cl | H | Cl | Cl | H | 147 – 148 |
| 149 | Cl | H | OH | H | H | Cl | Cl | H | H | 159 – 160 |
| 150 | H | Cl | OH | H | H | H | Cl | Cl | H | 121 – 122 |
| 151 | H | Cl | OH | Cl | H | H | H | H | H | 144 – 145 |
| 152 | H | Cl | OH | Cl | H | Cl | Cl | H | H | 162 – 163 |
| 153 | H | Cl | OH | Cl | H | $CH_3$ | H | H | H | 158 – 159 |
| 154 | H | Cl | OH | Cl | H | Cl | H | H | H | 139 – 140 |
| 155 | H | Cl | OH | H | Cl | Cl | H | H | H | 176 – 177 |
| 156 | Cl | H | OH | H | Cl | H | Cl | Cl | H | 197 – 198 |

EXAMPLE 2

6.7 g 2-hydroxy-3,5,6-trichlorophenylpropylketone were treated in a mixture of 10 ml water and 25 ml dioxane with 1.0 g sodium hydroxide to form the sodium salt. At 5°C 1.0 g of sodiumborohydride were then added and the reaction solution kept at 25°C for 5 hours with stirring. After this time the mixture was solidified with 2-N-hydrochloric acid and stirred for 1 further hour; from this the compound crystallised, precipitating first as an oil, of the formula fully.

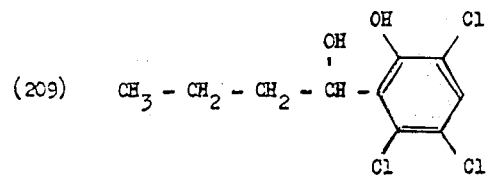

This was filtered off, washed with water, dried and recrystallised once from methylene chloride-hexane for purification; melting point 130°–131°C. The Pure yield amounts to 5.2 g.

In similar fashion the compounds given in the following table B can be prepared. The general formula for compounds of table B is:

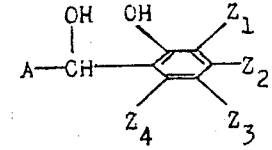

TABLE B

| Compound No. | A | $Z_1$ | $Z_2$ | $Z_3$ | $Z_4$ | Melting point in °C |
|---|---|---|---|---|---|---|
| 200 | $CH_3-$ | Cl | H | Cl | H | 55,5 – 56,5 |
| 201 | $CH_3-$ | H | Cl | Cl | H | 84 – 85 |
| 202 | $CH_3-$ | Br | H | Br | H | 82 – 83,5 |
| 203 | $CH_3-$ | Cl | H | Cl | Cl | 100 – 101 |
| 204 | $CH_3-CH_2-$ | Br | H | Br | H | 63 – 64 |
| 205 | $CH_3-CH_2-CH_2-$ | Cl | H | Cl | H | 45 – 46 |
| 206 | $CH_3-CH_2-CH_2-$ | Br | H | Br | H | 60 – 61 |
| 207 | $CH_3-CH_2-CH_2-$ | H | Cl | Cl | H | 64,5 – 65,5 |
| 208 | $CH_3-CH_2-CH_2-$ | H | Cl | H | Cl | 94 – 95 |
| 209 | $CH_3-CH_2-CH_2-$ | Cl | H | Cl | Cl | 130 – 131 |
| 210 | $CH_3-(CH_2)_3-CH_2-$ | Cl | H | Cl | H | 48 – 49 |
| 211 | $CH_3-$ | H | Cl | H | Cl | 77,5 – 78,5 |
| 212 | $CH_3-CH_2-$ | Cl | H | Cl | H | 46 – 47 |
| 213 | $CH_3-CH_2-$ | H | Cl | H | Cl | 102 – 103 |
| 214 | $CH_3{\rangle}CH-$ $CH_3$ | Cl | H | Cl | H | 54 – 55 |
| 215 | $CH_3-(CH_2)_2-CH_2-$ | Cl | H | Cl | H | 49 – 50 |
| 216 | $CH_3-(CH_2)_2-CH_2-$ | Br | H | Br | H | 66,5 – 67,5 |
| 217 | $CH_3-(CH_2)_2-CH_2-$ | H | Cl | Cl | H | 69,5 – 70,5 |
| 218 | $CH_3-(CH_2)_2-CH_2-$ | H | Cl | H | Cl | 77 – 78 |
| 219 | $CH_3-(CH_2)_2-CH_2-$ | Cl | H | Cl | Cl | 108 – 109 |
| 220 | $CH_3-(CH_2)_3-CH_2-$ | Cl | H | Cl | H | Oil |
| 221 | $CH_3-(CH_2)_3-CH_2-$ | Br | H | Br | H | 64 – 65 |
| 222 | $CH_3-(CH_2)_3-CH_2-$ | H | Cl | H | Cl | 64 – 65 |
| 223 | $CH_3-(CH_2)_3-CH_2-$ | Cl | H | Cl | Cl | 66,5 – 67,5 |
| 224 | $CH_3-(CH_2)_4-CH_2-$ | Cl | H | Cl | H | Oil |
| 225 | $CH_3-(CH_2)_4-CH_2-$ | H | Cl | H | Cl | 75,5 – 76,5 |
| 226 | $CH_3-(CH_2)_5-CH_2-$ | H | Cl | H | Cl | 73 – 74 |

EXAMPLE 3

Determination of the minimum inhibiting concentration (MIC) against bacteria and moulds by the gradient plates test Nos. 1) + 2)++

Gradient test 1 is given by W. Szybalski et al., Science 116, 26 (1952).

Gradient plate test 2 is that given by Nuesch and Knuesel, "Sideromycins", in the book by Gottlieb and Shaw, "Antibiotics, Mechanism of Action", volume 1 (1967), Springer Verlag.

The compounds of formulae 1 and 2 were mixed as suitable formulations (e.g. as solutions in dimethylsulfoxide) of given concentration with warm brain heart infusion-agar (bacteria) or mycophil-agar (moulds). The liquid mixtures were poured onto a solid wedge-shaped base agar layer and likewise allowed to solidify.

The test organism was then applied in a line perpendicular to the gradient with a pasteur pipette. After incubation for 24 hours at 37°C (bacteria) or 72 hours at 30°C (moulds) the length of the bacteria which had grown on the inoculation line was measured and expressed in parts per million of active agent. The results are given in the following tables C to F.

TABLE C

Minimum inhibiting concentration against *Staphylococcus aureus* (Bacteriostasis).

| Compound | MIC in ppm | Compound | MIC in ppm |
|---|---|---|---|
| 100 | 8 | 115 | 0,4 |
| 101 | 30 | 116 | 2 |
| 102 | 3 | 117 | 10 |
| 103 | 2 | 118 | 0,2 |
| 104 | 20 | 119 | 0,4 |
| 105 | 3 | 120 | 4 |
| 106 | 3 | 121 | 0,1 |
| 107 | 0,5 | 122 | 3 |
| 108 | 0,5 | 123 | 0,3 |
| 109 | 0,25 | 124 | 0,3 |
| 110 | 3 | 125 | 4 |
| 111 | 1 | 126 | 4 |
| 112 | 2 | 127 | 3 |
| 113 | 0,3 | 128 | 20 |
| 114 | 0,5 | 129 | 3 |
| 130 | 3 | 145 | 50 |
| 131 | 30 | 146 | 20 |
| 132 | 50 | 147 | 25 |
| 133 | 10 | 148 | 6 |
| 134 | 3 | 149 | 20 |
| 135 | 9 | 150 | 20 |
| 136 | 30 | 152 | 25 |
| 137 | 3 | 154 | 30 |
| 138 | 10 | 155 | 30 |
| 139 | 3,5 | 156 | 4 |
| 140 | 2 | 201 | 35 |
| 141 | 2 | 203 | 20 |
| 142 | 30 | 204 | 60 |
| 143 | 2 | 205 | 3 |
| 144 | 20 | 206 | 0,3 |

| Compound | MIC in ppm |
|---|---|
| 207 | 30 |
| 208 | 4 |
| 209 | 2 |
| 210 | 0,2 |
| 211 | 30 |
| 213 | 30 |
| 215 | 20 |
| 216 | 10 |
| 217 | 20 |
| 218 | 3 |
| 219 | 1 |
| 220 | 2 |
| 221 | 0,6 |
| 222 | 2 |
| 223 | 0,2 |
| 224 | 1 |
| 225 | 3 |
| 226 | 0,2 |

TABLE D

Minimum inhibiting concentration against *Escherichia coli* (Bacteriostasis).

| Compound | MIC in ppm | Compound | MIC in ppm |
|---|---|---|---|
| 101 | 20 | 117 | 40 |
| 102 | 20 | 119 | 20 |
| 103 | 10 | 120 | 40 |
| 104 | 50 | 122 | 15 |
| 105 | 35 | 126 | 10 |
| 106 | 40 | 127 | 40 |
| 108 | 30 | 128 | 50 |
| 109 | 15 | 130 | 20 |
| 110 | 20 | 131 | 70 |
| 111 | 20 | 133 | 60 |
| 112 | 25 | 135 | 30 |
| 113 | 30 | 136 | 66 |
| 114 | 30 | 137 | 40 |
| 115 | 10 | 138 | 50 |
| 116 | 20 | 140 | 30 |

| Compound | MIC in ppm |
|---|---|
| 141 | 20 |
| 142 | 40 |
| 143 | 30 |
| 149 | 50 |
| 150 | 45 |
| 154 | 50 |
| 156 | 50 |
| 201 | 50 |
| 203 | 40 |
| 205 | 40 |
| 206 | 35 |
| 207 | 40 |
| 208 | 30 |
| 209 | 30 |
| 213 | 30 |
| 215 | 40 |
| 216 | 20 |
| 217 | 20 |
| 218 | 10 |
| 222 | 10 |

TABLE E

Minimum inhibiting concentration against *Aspergillus niger* (Fungistasis).

| Compound | MIC in ppm | Compound | MIC in ppm |
|---|---|---|---|
| 100 | 30 | 119 | 10 |
| 101 | 60 | 120 | 50 |
| 102 | 40 | 122 | 25 |
| 103 | 20 | 126 | 30 |
| 104 | 50 | 127 | 30 |
| 105 | 30 | 129 | 40 |
| 106 | 20 | 130 | 25 |
| 108 | 20 | 133 | 60 |
| 110 | 30 | 135 | 45 |
| 111 | 20 | 136 | 60 |
| 112 | 40 | 140 | 40 |
| 113 | 40 | 142 | 60 |
| 115 | 10 | 143 | 40 |
| 116 | 15 | 144 | 70 |
| 117 | 55 | 145 | 20 |

| Compound | MIC in ppm |
|---|---|
| 148 | 15 |
| 149 | 40 |
| 150 | 40 |
| 152 | 55 |
| 156 | 20 |
| 203 | 30 |
| 206 | 80 |
| 207 | 90 |
| 208 | 40 |
| 209 | 10 |
| 213 | 40 |
| 215 | 70 |
| 216 | 50 |
| 217 | 50 |
| 218 | 20 |
| 219 | 10 |
| 220 | 60 |
| 221 | 30 |
| 222 | 20 |

TABLE F

Minimum inhibiting concentration against *Trichophyton mentagrophytes* (Fungistasis).

| Compound | MIC in ppm | Compound | MIC in ppm |
|---|---|---|---|
| 100 | 3 | 116 | 2 |
| 101 | 10 | 117 | 10 |
| 102 | 10 | 118 | 0,1 |
| 103 | 0,2 | 119 | 0,1 |

-continued

| Compound | MIC in ppm | Compound | MIC in ppm |
| --- | --- | --- | --- |
| 104 | 4 | 120 | 4 |
| 105 | 4 | 121 | 4 |
| 106 | 2 | 122 | 4 |
| 107 | 1 | 123 | 0,2 |
| 108 | 0,3 | 124 | 30 |
| 110 | 4 | 125 | 4 |
| 111 | 0,3 | 126 | 3 |
| 112 | 3 | 127 | 3 |
| 113 | 3 | 128 | 20 |
| 114 | 1 | 129 | 3 |
| 115 | 0,4 | 130 | 1 |
| 131 | 10 | 148 | 4 |
| 132 | 10 | 149 | 10 |
| 133 | 4 | 150 | 5 |
| 134 | 1 | 151 | 30 |
| 135 | 7 | 152 | 10 |
| 136 | 10 | 153 | 30 |
| 137 | 3 | 154 | 2 |
| 138 | 3 | 155 | 10 |
| 139 | 2 | 156 | 4 |
| 140 | 1 | 201 | 20 |
| 141 | 1 | 203 | 4 |
| 142 | 5 | 204 | 10 |
| 143 | 3 | 205 | 30 |
| 144 | 10 | 206 | 10 |
| 145 | 10 | 207 | 5 |

| Compound | MIC in ppm |
| --- | --- |
| 208 | 2 |
| 209 | 2 |
| 210 | 0,4 |
| 212 | 0,5 |
| 213 | 5 |
| 215 | 20 |
| 216 | 4 |
| 217 | 10 |
| 218 | 0,4 |
| 219 | 0,3 |
| 220 | 20 |
| 221 | 0,1 |
| 222 | 0,4 |
| 223 | 2 |
| 224 | 3 |
| 225 | 1 |
| 226 | 10 |

EXAMPLE 4

A specimen of 140 g cotton-poplin was impregnated at 20°C for 7 minutes in a bath of the following composition:
1000 ml water
2.7 ml cloth softening rinsing dye (containing 7% of a mixture of di-octadecyl and di-hexadecyl-dimethylammonium chloride)
15 mg of the compound of formula (109) (added as a solution in 0.5 ml dimethylsulfoxide)

The so treated cloth specimen was squeezed out after 100% dyebath take up and then dried at 45°C.

For testing the action against bacteria, roundels of 20 mm diameter were cut from the impregnated cloth and laid on brain-heart infusion agar plates, which had been pre-infected with Staphylococcus aureus. The plates were then incubated for 24 hours at 37°C.

Two observations were made, that of the zone of inhibition arising around the roundels (inhibition zone in mm) and the determinable growth (%) above or below the cloth. The inhibition zone was only a trace quantity while the determinable growth was 0%.

Similar effects were obtained with further compounds of formula 1 or 2.

EXAMPLE 5

For the manufacture of an anti-microbial tablet of soap, 2.4 g of one of the compounds of Formula 1 or 2 were added to the following mixture:

120 g natural soap in flake form
0.12 g disodium salt of ethylenediaminetetraacetic acid (dihydrate)
0.24 g titanium dioxide.

The soap shavings obtained by rolling were powdered with a high speed mixture and then pressed to soap tablet form.

Concentrated aqueous solutions of the anti-microbial soaps were mixed into warm brain heart infusion agar so that in-corporation dilution rose with 2, 10, 20, 100 etc. parts per million active agent were produced. The warm mixtures were poured into petri dishes, allowed ot solidify and then infected with staphylococcus aureus.

After 24 hour incubation at 37°C the minimum inhibiting concentration was determined. The results are shown in the following table. Similar results were obtained by the use of other compounds of formulae 1 and 2.

| Compound No. | Minimum inhibiting concentration of the anti-microbial soap in p.p.m. active agent |
| --- | --- |
| 104 | $\leq 20$ |
| 105 | $\leq 20$ |
| 106 | $\leq 20$ |
| 108 | $\leq 2$ |
| 109 | $\leq 2$ |

EXAMPLE 6

Specimens of 100 g cotton-cretonne were impregnated on the foulard with 1% solutions of compounds of formula 1 in isopropanol at 20°C and the squeezed out with 100% bath take-up.

In the same way, samples of 100 g wool cheviot were treated.

The textiles which were dried at 30 to 40°C contained 1% by weight of active agent taken on their own weight.

For testing the action against bacteria, roundels of 10 mm diameter cut from the impregnated cloth, dewatered and watered, were laid for 24 hours at 29°C on brain heart infusion agar plates which had been previously infected with Staphylococcus aureus. The plates were then incubated for 18 hours at 37°C.

Two factors were observed: first, the inhibition zone (in mm) arising round the roundels and second, the microscopically determinable growth (in %) under or on the cloth.

Results are expressed in the following table; similar results were obtained also with further compounds of formulae 1 and 2

| Substrate (with 1% active agent) | Compound | unwatered | | watered | |
| --- | --- | --- | --- | --- | --- |
| | | Inhibition zone (mm) | Growth (%) | Inhibition zone (mm) | Growth (%) |
| Cotton | 103 | 8 | 0 | 9 | 0 |
| | 108 | 5 | 0 | 4 | 0 |
| | 115 | 9 | 0 | 5 | 0 |
| | 116 | 8 | 0 | 5 | 0 |
| | 152 | 4 | 0 | 2 | 0 |
| Wool | 103 | 5 | 0 | 2 | 0 |
| | 108 | 3 | 0 | 4 | 0 |
| | 115 | 6 | 0 | 5 | 0 |
| | 116 | 5 | 0 | 5 | 0 |

-continued

| Substrate (with 1% active agent) | Compound | unwatered Inhibition zone (mm) | Growth (%) | watered Inhibition zone (mm) | Growth (%) |
| --- | --- | --- | --- | --- | --- |
| | 152 | Trace | 0 | 2 | 0 |

EXAMPLE 7

Substantivity tests with calf-hide roundels

Calf-hide roundels of 10 mm diameter were dipped for 2 minutes in 8% aqueous solutions of the antimicrobial soaps produced according to Example 4. After 3 minutes rinsing in flowing water, the roundels were laid on brain-heart infusion agar plates which had been pre-infected with *Staphylococcus aureus*. Finally the plates were incubated for 20 hours at 37°C.

The zone of inhibition arising around the calf-hide roundels was observed in mm and the microscopically determinable growth under or on the roundels was determined in %. Results are as follows:

| Soap with Compound No. | Inhibition zone in mm | Growth in % |
| --- | --- | --- |
| 105 | 1 | 0 |
| 109 | 1 | 0 |

Similar values were obtained using other compounds of formulae 1 and 2.

EXAMPLE 8

The following mixture was milled on the twin-roll mill at 150°C for 20 minutes:
  100.00 g polyvinylchloride
  19.20 g di-(2-ethyl-hexyl-phthalate)
  27.00 g di-(2-ethyl-hexyl-sebacate)
  1.50 g Ba/Cd-laurate
  0.25 g Stearic acid
  7.80 g of a solution of 3.10 g of a compound of formula 1 in 4.70 g di-(2-ethyl-hexyl-phthalate)

The roll separation was adjusted so that 1 mm thick sheets were formed which were then pressed for 20 minutes at 165°–170°C under a pressure of 1,400 kg/cm².

For testing the action against bacteria, discs of 10 mm diameter were stamped from the rolled soft polyvinylchloride sheet and laid on brain-heart infusion agar plates which had previously been infected with *Staphyloccocus aureus*. The plates were then incubated for 24 hours at 37°C.

The zone of inhibition arising round the discs was measured in mm and the microscopically determinable growth above and below the soft polyvinylchloride was measure in %.

The results are given in the following table: Similar action is observed with other compounds of formulae 1 and 2.

| Compound No. | Zone of Inhibition (mm) | Growth (%) |
| --- | --- | --- |
| 106 | Trace | 0 |
| 108 | 3 | 0 |
| 115 | 2 | 0 |
| 156 | 2 | 0 |

We claim:

1. A method of combating bacteria or fungi which comprises applying thereto a bactericidally or fungicidally effective amount of a compound of the formula

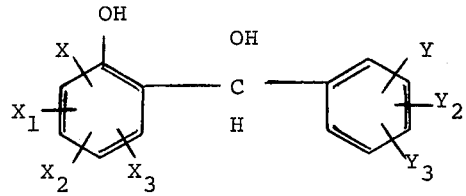

wherein X is halogen; each of $X_1$, $X_2$, $X_3$ is hydrogen or halogen; Y is hydrogen, halogen or methyl; each of $Y_2$ and $Y_3$ are hydrogen or halogen and wherein at least two of $X_1$, $X_2$, $X_3$, Y, $Y_2$ and $Y_3$ are not hydrogen.

2. The method according to claim 1 in which the compound is

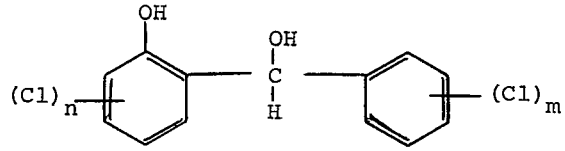

wherein $n$ is 2, 3 or 4; $m$ is 1, 2 or 3; and the sum of $n$ and $m$ is 3, 4 or 5.

3. The method according to claim 2 in which the compound is 2-hydroxy-3,3',4',5,6-pentachlorobenzhydrol.

4. The method according to claim 2 in which the compound is 2-hydroxy-3',4,4',6-tetrachlorobenzhydrol.

5. The method according to claim 1 in which the compound is 2-hydroxy-3,5,6-trichlorobenzhydrol.

6. The method according to claim 2 in which the compound is 2-hydroxy-2',4,4',6-tetrachlorobenzhydrol.

7. The method according to claim 2 in which the compound is 2-hydroxy-3,4',5,6-tetrachlorobenzhydrol.

8. The method according to claim 2 in which the compound is 2-hydroxy-3,3',4',5-tetrachlorobenzhydrol.

9. A method for protecting organic materials against the action of bacteria or fungi, which comprises impregnating said material or applying to the surface of said material a bactericidally or fungicidally effective amount of a compound of the formula

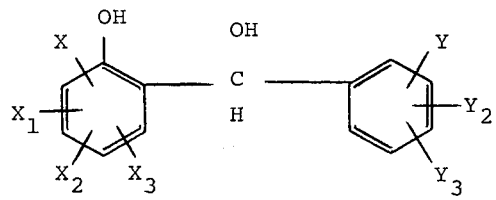

wherein X is halogen; each of $X_1$, $X_2$ and $X_3$ is hydrogen or halogen; Y is hydrogen, halogen or methyl; each of $Y_2$ and $Y_3$ are hydrogen or halogen; and wherein at least two of $X_1$, $X_2$, $X_3$, Y, $Y_2$ and $Y_3$ are not hydrogen.

10. The method according to claim 9 in which the compound is

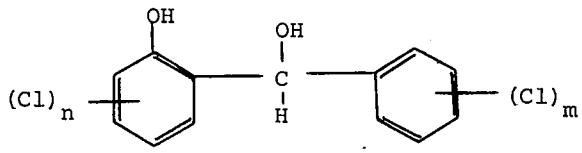

wherein $n$ is 2, 3 or 4; $m$ is 1, 2 or 3; and the sum of $n$ and $m$ is 3, 4 or 5.

11. The method according to claim 10 in which the compound is 2-hydroxy-3,3',4',5,6-pentachlorobenzhydrol.

12. The method according to claim 10 in which the compound is 2-hydroxy-3',4,4',6-tetrachlorobenzhydrol.

13. The method according to claim 9 in which the compound is 2-hydroxy-3,5,6-trichlorobenzhydrol.

14. The method according to claim 10 in which the compound is 2-hydroxy-2',4,4',6-tetrachlorobenzhydrol.

15. The method according to claim 10 in which the compound is 2-hydroxy-3,4',5,6-tetrachlorobenzhydrol.

16. The method according to claim 10 in which the compound is 2-hydroxy-3,3',4',5-tetrachlorobenzhydrol.

17. A composition for combating bacteria or fungi comprising (1) a fungicidally or bacterially effective amount of a compound of the formula

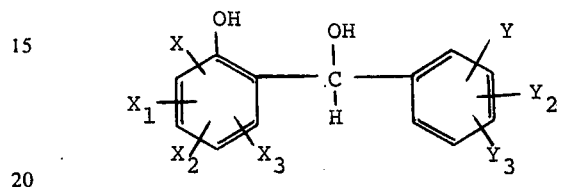

wherein X is halogen; each of $X_1$, $X_2$ and $X_3$ is hydrogen or halogen; Y is hydrogen, halogen or methyl; each of $Y_2$ and $Y_3$ are hydrogen or halogen; and wherein at least two of $X_1$, $X_2$, $X_3$, Y, $Y_2$ and $Y_3$ are not hydrogen; and (2) a carrier.

* * * * *